(12) United States Patent
Tian et al.

(10) Patent No.: US 11,492,607 B2
(45) Date of Patent: Nov. 8, 2022

(54) HIGHLY ACTIVE S-CYANOHYDRIN LYASE AND APPLICATION THEREOF

(71) Applicant: Abiochem Biotechnology Co., Ltd., Shanghai (CN)

(72) Inventors: Zhenhua Tian, Shanghai (CN); Zhanbing Cheng, Shanghai (CN); Chuanmin Sun, Shanghai (CN)

(73) Assignee: ABIOCHEM BIOTECHNOLOGY CO., LTD., Shanghai (CN)

( * ) Notice: Subject to any disclaimer, the term of this patent is extended or adjusted under 35 U.S.C. 154(b) by 389 days.

(21) Appl. No.: 16/476,349

(22) PCT Filed: Jan. 5, 2018

(86) PCT No.: PCT/CN2018/071619
§ 371 (c)(1),
(2) Date: Jul. 8, 2019

(87) PCT Pub. No.: WO2018/127143
PCT Pub. Date: Jul. 12, 2018

(65) Prior Publication Data
US 2021/0403893 A1    Dec. 30, 2021

(30) Foreign Application Priority Data

Jan. 6, 2017 (CN) .......... 201710011396.3
Sep. 1, 2017 (CN) .......... 201710777767.9
Dec. 8, 2017 (CN) .......... 201711295257.4

(51) Int. Cl.
*C12N 9/88* (2006.01)
*C12N 1/16* (2006.01)
(Continued)

(52) U.S. Cl.
CPC .............. *C12N 9/88* (2013.01); *C12N 1/16* (2013.01); *C12N 1/20* (2013.01); *C12P 13/004* (2013.01); *C12Y 401/02037* (2013.01)

(58) Field of Classification Search
None
See application file for complete search history.

(56) References Cited

U.S. PATENT DOCUMENTS

2021/0403893 A1* 12/2021 Tian ............. C12P 13/004

FOREIGN PATENT DOCUMENTS

| CN | 102899306 A | 1/2013 |
|----|-------------|--------|
| CN | 106032531 A | 10/2016 |
| WO | 2005095602 A1 | 10/2005 |

OTHER PUBLICATIONS

GenBank Accession No. CAA11219.1, published Nov. 14, 2006 (Year: 2006).*

(Continued)

*Primary Examiner* — Richard C Ekstrom
(74) *Attorney, Agent, or Firm* — Panitch Schwarze Belisario & Nadel LLP

(57) ABSTRACT

The invention provides a highly active S-cyanohydrin lyase obtained by mutating an amino acid residue at position 103 of a wild-type cassava S-cyanohydrin lyase. The mutation can significantly increase an expression of a mutant enzyme in *E. coli* and does not require a decrease in temperature when induced. Further mutations at position 128 and other sites were performed to obtain mutants with increased catalytic activity.

8 Claims, 1 Drawing Sheet
Specification includes a Sequence Listing.

(51) Int. Cl.
*C12N 1/20* (2006.01)
*C12P 13/00* (2006.01)

(56) References Cited

OTHER PUBLICATIONS

PIR Accession No. T50818, published Jul. 21, 2000 (Year: 2000).*
Int'l Search Report dated Apr. 8, 2018 in Int'l Application No. PCT/CN2018/071619.
Dadashipour et al, "7 Chain A, Crystal Structure Of S-Hydroxynitrile Lyase From Ma Esculenta (His103leu)," GenBank Database Register No. 4YK7_A (Apr. 14, 2016).

* cited by examiner

HIGHLY ACTIVE S-CYANOHYDRIN LYASE AND APPLICATION THEREOF

CROSS-REFERENCE TO RELATED APPLICATION

This application is a Section 371 of International Application No. PCT/CN2018/071619, filed Jan. 5, 2018, which was published in the Chinese language on Jul. 12, 2018, under International Publication No. WO 2018/127143 A1, which claims priority under 35 U.S.C. § 119(b) to Chinese Application No. 2017-10011396.3, filed Jan. 6, 2017, Chinese Application No. 2017-10777767.9, filed Sep. 1, 2017 and Chinese Application No. 2017-11295257.4, filed Dec. 8, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing_688457-52.txt", creation date of Jul. 8, 2019, and having a size of about 15.4 KB The sequence listing submitted via EFS-Web is part of the specification and is herein incorporated by reference in its entirety.

TECHNICAL FIELD

The present invention relates to the field of biotechnology, and in particular, the present invention relates to a highly active S-cyanohydrin lyase and application thereof.

BACKGROUND

Cyanohydrin lyase is an industrial enzyme that is very useful in chemical production. Its natural activity is to catalyze the cleavage of cyanohydrin and release hydrocyanic acid. The cyanohydrin lyase can catalyze reverse reaction, i.e., the addition of HCN to aldehyde ketone, to obtain an optically active α-cyanohydrin product. S-type cyanohydrin (SCMB) of m-phenoxybenzaldehyde (m-PBAld) is a key intermediate for pyrethroid pesticides. The traditional chemical method has the problem of low stereoselectivity, while the production process of SCMB catalyzed by S-cyanohydrin lyase has the selectivity.

Natural S-cyanohydrin lyase is present in a few plant tissues such as rubber, cassava and sorghum, with low abundance and difficulty in purification. In 1995, Wajant isolated the cassava cyanohydrin lyase MeHNL from cassava by five-step purification method (Plant Sci., 1995, 108, 1); White et al. extracted MeHNL from cassava leaves using three-step method and obtained enzyme solution by means of salting out and dialysis, but the stereoselectivity of the enzyme applied in chemical catalysis was not high (Plant Physiol 1998, 116, 1219). The cyanohydrin lyase (MeHNL) derived from *Manihot esculenta* is an S-cyanohydrin lyase. It has been reported that MeHNL can catalyze the chemical synthesis of S-type chiral cyanohydrin with an ee value of >99%. The lyase has high application value, but the enzyme activity is still not high enough to meet the requirements of practical application.

Therefore, the skilled in the art are working to develop a S-cyanohydrin lyase with higher activity to reduce the application cost.

SUMMARY OF THE INVENTION

It is an object of the present invention to provide a highly active S-cyanohydrin lyase and application thereof.

In a first aspect of the invention, a mutated S-cyanohydrin lyase is provided, which is mutated at one or more sites selected from the group consisting of: amino acid residue of position 103, amino acid residue of position 128, amino acid residue of position 2, amino acid residue of position 81, amino acid residue of position 149, amino acid residue of position 94, and amino acid residue of position 176, wherein the amino acid residues are numbered as shown in SEQ ID NO. 1.

In another preferred embodiment, the catalytic activity of the mutated S-cyanohydrin lyase is increased by more than 30%; preferably increased by more than 50%; more preferably increased by more than 80% compared to that of the wild-type S-cyanohydrin lyase.

In another preferred embodiment, the catalytic activity of the mutated S-cyanohydrin lyase is at least 2 times; preferably at least 5 times; more preferably at least 10 times, of that of the wild-type S-cyanohydrin lyase.

In another preferred embodiment, the amino acid sequence of the wild-type S-cyanohydrin lyase is as shown in SEQ ID NO.1.

In another preferred embodiment, the amino acid sequence of the mutated S-cyanohydrin lyase has at least 80% homology to SEQ ID NO. 1; more preferably, has at least 90% homology, most preferably, has at least 95% homology; such as has at least 96%, 97%, 98%, 99% homology.

In another preferred embodiment, the mutation sites of the mutated S-cyanohydrin lyase comprise amino acid residue of position 103; preferably, the amino acid residue of position 103 is mutated from H to L, I, V, C, S or M.

In another preferred embodiment, the mutation sites of the mutated S-cyanohydrin lyase further comprise amino acid residue of position 128; preferably, the amino acid residue of position 128 is mutated from W to A, N, L, V, G or Y, more preferably, the amino acid residue of position 128 is mutated from W to A.

In another preferred embodiment, the mutation sites of the mutated S-cyanohydrin lyase further comprise amino acid residue of position 2; preferably, the amino acid residue of position 2 is mutated from V to P, L, D, I, G, H, R, M, S, C, W, T, Q, or A.

In another preferred embodiment, the mutation sites of the mutated S-cyanohydrin lyase further comprise amino acid residue of position 81; preferably, the amino acid residue of position 81 is mutated from C to A, V or I.

In another preferred embodiment, the mutation sites of the mutated S-cyanohydrin lyase further comprise amino acid residue of position 149; preferably, the amino acid residue of position 149 is mutated from L to I, C, A or P.

In another preferred embodiment, the mutation sites of the mutated S-cyanohydrin lyase further comprise amino acid residue of position 94; preferably, the amino acid residue of position 94 is mutated from V to P, R, S, K.

In another preferred embodiment, the mutation sites of the mutated S-cyanohydrin lyase further comprise amino acid residue of position 176; preferably, the amino acid residue of position 176 is mutated from K to P.

In another preferred embodiment, the mutated S-cyanohydrin lyase is further mutated at one or more sites selected from the group consisting of: amino acid residue of position 209, amino acid residue of position 94, amino acid residue of position 165, amino acid residue of position 140, amino acid residue of position 224, amino acid residue of position 173, and amino acid residue of position 36, wherein the amino acid residues are numbered as shown in SEQ ID NO. 1.

In another preferred embodiment, the mutation sites of the mutated S-cyanohydrin lyase further comprise amino acid residue of position 209; preferably, the amino acid residue of position 209 is mutated from K to R, A, S, C, G, M, L, F, S, or C.

In another preferred embodiment, the mutation sites of the mutated S-cyanohydrin lyase further comprise amino acid residue of position 94; preferably, the amino acid residue of position 94 is mutated from V to P, S, C, G, R, K, S, A, F, or T.

In another preferred embodiment, the mutation sites of the mutated S-cyanohydrin lyase further comprise amino acid residue of position 165; preferably, the amino acid residue of position 165 is mutated from G to P, D, S, or T.

In another preferred embodiment, the mutation sites of the mutated S-cyanohydrin lyase further comprise amino acid residue of position 140; preferably, the amino acid residue of position 140 is mutated from T to H, G, K, I, D, W, S, or R.

In another preferred embodiment, the mutation sites of the mutated S-cyanohydrin lyase further comprise amino acid residue of position 224; preferably, the amino acid residue of position 224 is mutated from K to P, E, V, S, I, H, D, N, A, or T.

In another preferred embodiment, the mutation sites of the mutated S-cyanohydrin lyase further comprise amino acid residue of position 173; preferably, the amino acid residue of position 173 is mutated from V to Q, L, S, A, C, I, or T.

In another preferred embodiment, the mutation sites of the mutated S-cyanohydrin lyase further comprise amino acid residue of position 36; preferably, the amino acid residue of position 36 is mutated from L to A, F, I.

In another preferred embodiment, the mutation sites of the mutated S-cyanohydrin lyase comprise amino acid residue of position 128 and amino acid residue of position 103.

In another preferred embodiment, the mutation sites of the mutated S-cyanohydrin lyase comprise amino acid residue of position 128 and amino acid residue of position 103; and the mutated S-cyanohydrin lyase is mutated at one or more sites selected from the group consist of: amino acid residue of position 2, amino acid residue of position 81, amino acid residue of position 149, amino acid residue of position 176, amino acid residue of position 209, amino acid residue of position 94, amino acid residue of position 165, amino acid residue of position 140, amino acid residue of position 224, amino acid residue of position 173, and amino acid residue of position 36, wherein the amino acid residues are numbered as shown in SEQ ID NO. 1.

In another preferred embodiment, the number of mutation sites in the mutated S-cyanohydrin lyase is 1-5, preferably 2-4, such as 3.

In another preferred embodiment, the mutated S-cyanohydrin lyase is selected from specific mutated enzymes in Table 2.

In another preferred embodiment, the mutated S-cyanohydrin lyase comprises mutations in the sites of specific mutated enzymes in Table 2.

In another preferred embodiment, the mutated S-cyanohydrin lyase is selected from the mutant enzymes 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138 or 139, in Table 2.

In another preferred embodiment, the mutated S-cyanohydrin lyase comprises mutation sites selected from the group consisting of:

| Mutant enzyme number | Mutation site |
|---|---|
| 3 | L36A, H103L, W128A |
| 4 | V94E, H103L, W128A |
| 5 | L36C, H103L, W128A |
| 6 | L36Y, H103L, W128A |
| 9 | V94L, H103L, W128A |
| 10 | L36Q, H103L, W128A |
| 13 | C81Y, H103L, W128A |
| 18 | V94Q, H103L, W128A |
| 20 | V94H, H103L, W128A |
| 21 | H103L, W128A, V173T |
| 22 | C81Y, H103L, W128A |
| 27 | C81V, H103L, W128A |
| 29 | H103L, W128A, V173I |
| 30 | V94T, H103L, W128A |
| 31 | H103L, W128A, V173C |
| 34 | H103L, W128A, 149A |
| 35 | V94F, H103L, W128A |
| 36 | H103L, W128A, V173A |
| 37 | L36I, H103L, W128A |
| 38 | H103L, W128A, V173S |
| 39 | L36F, H103L, W128A |
| 40 | H103S |
| 41 | C81I, H103L, W128A |
| 42 | V94A, H103L, W128A |
| 43 | V2P, H103L, W128A |
| 44 | V2W, H103L, W128A |
| 45 | V2T, H103L, W128A |
| 46 | V94S, H103L, W128A, K209R |
| 47 | H103L, W128A, V173L, K209C |
| 48 | V94R, H103L, W128A, K209C |
| 49 | H103V |
| 50 | H103L, W128A, G165T |
| 51 | H103L, W128A, V173L, K209S |
| 52 | V2H, H103L, W128A |
| 53 | H103L, W128A, K224T |
| 54 | V2D, H103L, W128A |
| 55 | V94G, H103L, W128A |
| 56 | V2P, C81A H103L, W128A, L149C |
| 57 | V2S, H103L, W128A |
| 58 | H103L, W128A, K224A |
| 59 | V2Q, H103L, W128A |
| 60 | H103L, W128A, K199P, K176P |
| 61 | V2R, H103L, W128A |
| 62 | V94R, H103L, W128A, V173L |
| 63 | H103I |
| 64 | H103L, W128A, K199P |
| 65 | H103L, W128A, K176P |
| 66 | V94C, H103L, W128A |
| 67 | H103L, W128A, K224N |
| 68 | H103L, W128A, K224D |
| 69 | V94S, H103L, W128A, V173L |
| 70 | H103L, W128A, K199P, K224P |
| 71 | V2C, H103L, W128A |
| 72 | H103L, W128A |
| 73 | H103L, W128A, K224P |
| 74 | H103L, W128A, V173L |
| 75 | H103L, W128A, K224H |
| 76 | H103L, W128A, K224I |
| 77 | H103L, W128A, K224S |
| 78 | H103L, W128A, K224V |
| 79 | H103L, W128A, G165S |
| 80 | H103L, W128A, K176P, K224P |
| 81 | H103C |
| 82 | H103L, W128A, V173Q |
| 83 | H103L, W128A, K224E |
| 84 | V94S, H103L, W128A, K209C |
| 85 | H103L, W128A, K224P |
| 86 | H103L, W128A, T140R |
| 87 | H103L |
| 88 | H103L, W128A, T140S |
| 89 | H103L, W128A, T140W |
| 90 | H103L, W128A, T140D |
| 91 | V94S, H103L, W128A, G165D |
| 92 | H103L, W128A, T140I |

-continued

| Mutant enzyme number | Mutation site |
| --- | --- |
| 93 | H103L, W128A, T140K |
| 94 | H103L, W128A, G165P |
| 95 | H103L, W128A, T140G |
| 96 | H103L, W128A, T140H |
| 97 | V94R, H103L, W128A |
| 98 | H103L, W128A, K209F |
| 99 | H103L, W128A, G165D |
| 100 | V94R, H103L, W128A, K209R |
| 101 | V94R, H103L, W128A, G165D |
| 102 | V94S, H103L, W128A |
| 103 | H103L, W128A, K209L |
| 104 | C81A, H103L, W128A |
| 105 | H103L, W128A, K209M |
| 106 | H103L, W128A, K209G |
| 107 | H103L, W128A, K209A |
| 108 | H103L, W128A, K209S |
| 109 | H103L, W128A, K209C |
| 110 | C81A, H103L, W128A, K224P |
| 111 | C81A, H103L, W128A |
| 112 | H103L, W128A, K209R |
| 113 | V2I, H103L, W128A |
| 114 | C81A, H103L, W128A, K176P |
| 115 | V2A, C81A, H103L, W128A, L149C |
| 116 | L36A, H103L, W128A |
| 117 | V2G, C81A, H103L, W128A |
| 118 | V2L, C81A, H103L, W128A |
| 119 | V2P, C81A, H103L, W128A |
| 120 | V2H, C81A, H103L, W128A |
| 121 | V2R, C81A, H103L, W128A |
| 122 | V2M, C81A, H103L, W128A |
| 123 | V2S, C81A, H103L, W128A |
| 124 | V2C, C81A, H103L, W128A |
| 125 | V2W, C81A, H103L, W128A |
| 126 | V2T, C81A, H103L, W128A |
| 127 | V2Q, C81A, H103L, W128A |
| 128 | V2A, C81A, H103L, W128A |
| 129 | C81A, H103L, W128A, L149P |
| 130 | C81A, H103L, W128A, L149I |
| 131 | C81A, H103L, W128A, L149C |
| 132 | C81A, V94P, H103L, W128A, K176P |
| 133 | C81A, 94R, H103L, W128A, L149P |
| 134 | C81A, 94K, H103L, W128A, L149P |
| 135 | V2P, C81A, H103L, W128A, L149C |
| 136 | H103I, W128A |
| 137 | H103V, W128A |
| 138 | H103C, W128A |
| 139 | H103S, W128A |
| 140 | H103I, W128Y |
| 141 | H103L, W128N |
| 142 | H103L, W128G |
| 143 | H103L, W128Y |
| 144 | H103I, W128N |
| 145 | H103I, W128G |
| 146 | H103C, W128V |
| 147 | H103C, W128G |
| 148 | H103C, W128Y; and |
| 149 | 103M, W128L. |

In a second aspect of the invention, a polynucleotide molecule is provided, encoding the mutated S-cyanohydrin lyase of the first aspect of the invention.

In a third aspect of the invention, a vector is provided, comprising the nucleic acid molecule of the second aspect of the invention.

In a fourth aspect of the invention, a host cell is provided, comprising the vector of the first aspect of the invention or having the nucleic acid molecule of the second aspect of the invention integrated into its genome.

In another preferred embodiment, the host cell is a prokaryotic cell, or a eukaryotic cell.

In another preferred embodiment, the prokaryotic cell is *Escherichia coli*.

In a fifth aspect of the invention, a method for preparing the mutated S-cyanohydrin lyase of the first aspect of the invention is provided, comprising the steps of:

(i) culturing the host cell of the fourth aspect of the invention under suitable conditions to express the mutated cyanohydrin lyase; and (ii) isolating the mutated cyanohydrin lyase.

In another preferred embodiment, in the step (i), the culture temperature of the host cell is 20° C.-40° C.; preferably 25° C.-37° C., such as 35° C.

In a sixth aspect of the invention, an enzyme preparation is provided, comprising the mutated S-cyanohydrin lyase of the first aspect of the invention.

In a seventh aspect of the invention, it provides a use of the mutated S-cyanohydrin lyase of the first aspect of the invention or the enzyme preparation of the sixth aspect of the invention, for preparing an optically active S-cyanohydrin product.

In another preferred embodiment, the use further comprises catalyzing the addition reaction of HCN with aldehyde ketone.

In an eighth aspect of the invention, a method for the preparation of S-cyanohydrin is provided, comprising the steps of:

(1) contacting the mutated S-cyanohydrin lyase of the first aspect of the invention with a reaction substrate to carry out a catalytic reaction, thereby producing the S-cyanohydrin;

(2) isolating and purifying the S-cyanohydrin product.

In another preferred embodiment, in step (1), the reaction substrate comprises m-phenoxybenzaldehyde, HCN (or sodium cyanide/potassium cyanide), and/or acetone cyanohydrin.

In another preferred embodiment, in step (1), the temperature of the catalytic reaction is 0-20° C.

It should be understood that, in the present invention, each of the technical features specifically described above and below (such as those in the Examples) can be combined with each other, thereby constituting new or preferred technical solutions, which needs not be described one by one, due to space limitations.

EMBODIMENTS FOR CARRYING OUT THE PRESENT INVENTION

Figure 1:
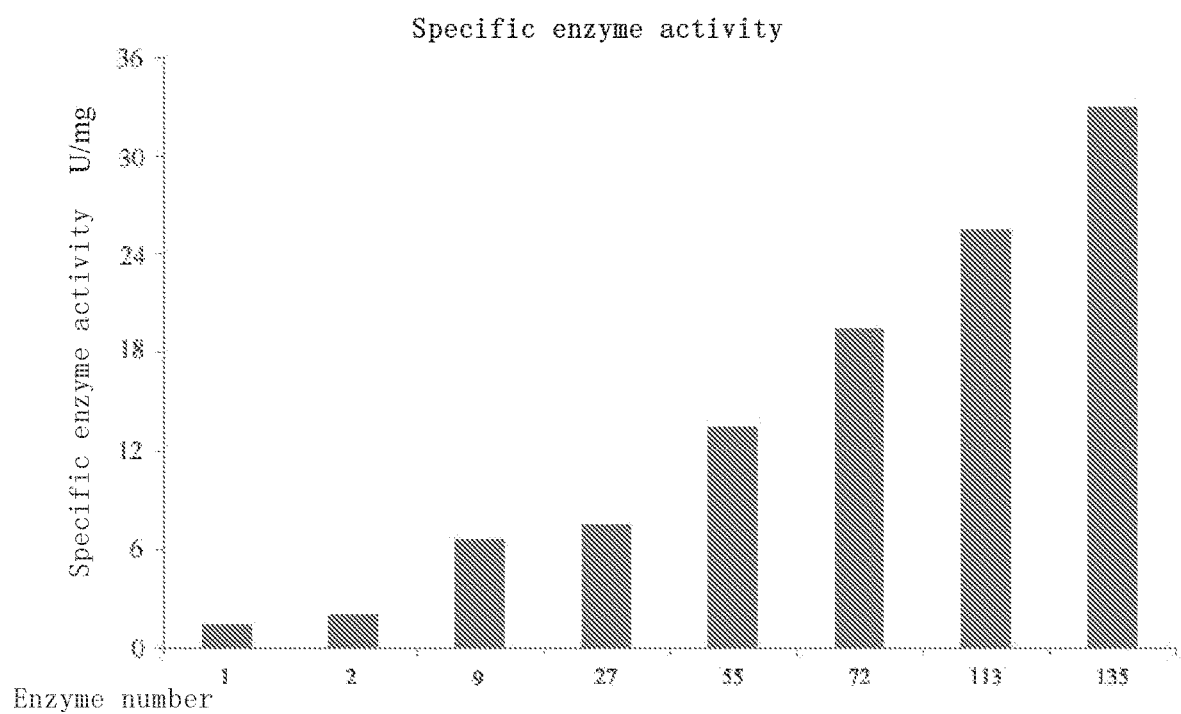
FIG. 1 shows the results of specific enzyme activity determination of wild type and some of the typical mutants of the invention.

After extensive and intensive studies, the inventors have unexpectedly discovered that mutation at amino acid residue of position 103 of the wild-type S-cyanohydrin lyase can significantly increase the expression of the mutant enzyme in *E. coli*. In addition, it is not needed to reduce the temperature during the induction of expression, which significantly reduces the preparation cost of the enzyme. Further, mutations at other sites such as position 128 can obtain an S-cyanohydrin lyase with improved catalytic activity. The experimental results showed that the catalytic activity of the mutated S-cyanohydrin in the addition reaction of m-phenoxybenzaldehyde (m-PBAld) with HCN was increased by more than 30% compared with that of the wild type. On this basis, the inventors completed the present invention.

Before describing the present invention, it should be understood that the invention is not limited to the specific methods and experimental conditions described, as such methods and conditions may be changed. It is also understood that the terms used herein are only for the purpose of describing specific embodiments and are not intended to be restrictive. The scope of the invention will be limited only by the appended claims.

Unless otherwise defined, all technical and scientific terms used herein have the same meaning as commonly understood by the skilled in the art of the invention. As used herein, when used in reference to a particular recited value, the term "about" means that the value can vary by no more than 1% from the recited value. For example, as used herein, the expression "about 100" comprises all values between 99 and 101 (e.g., 99.1, 99.2, 99.3, 99.4, etc.).

Although any methods and materials similar or equivalent to those described in the present invention can be used in the practice or testing of the invention, the preferred methods and materials are exemplified herein.

Cyanohydrin Lyase

Cyanohydrin lyase (Hydroxynitrile lyase) is mainly derived from a few plant tissues such as rubber, cassava and sorghum, which mainly comprises: cassava cyanohydrin lyase (MeHNL), lacquer tree cyanohydrin lyase (HbHNL), and almond cyanohydrin lyase (PaHNL).

In a preferred embodiment of the invention, the cyanohydrin lyase is cassava cyanohydrin lyase.

In a preferred embodiment of the invention, preferably, the sequence of wild type cassava cyanohydrin lyase is as follow:

```
                                                    SEQ ID NO.: 1
MVTAHFVLIH TICHGAWIWH KLKPALERAG HKVTALDMAA SGIDPRQIEQ INSFDEYSEP   60

LLTFLEKLPQ GEKVIIVGES CAGLNIAIAA DRYVDKIAAG VFHNSLLPDT VHSPSYTVEK  120

LLESFPDWRD TEYFTFTNIT GETITTMKLG FVLLRENLFT KCTDGEYELA KMVMRKGSLF  180

QNVLAQRPKF TEKGYGSIKK VYIWTDQDKI FLPDFQRWQI ANYKPDKVYQ VQGGDHKLQL  240

TKTEEVAHIL QEVADAYA                                                258
```

The wild-type coding gene sequence is as follow:

```
                                            (SEQ ID NO. 2)
ATGGTTACTGCACACTTCGTTCTGATTCACACCATTTGTCACGGCGCAT

GGATTTGGCACAAACTGAAACCGGCCCTGGAACGTGCTGGCCACAAAGT

TACTGCACTGGACATGGCAGCCAGTGGCATTGACCCGCGTCAAATTGAA

CAGATCAACTCTTTCGATGAATACTCTGAACCGCTGCTGACTTTCCTGG

AAAAACTGCCGCAAGGCGAAAAGGTTATCATTGTTGGTGAAAGCTGTGC

AGGCCTGAACATTGCTATTGCTGCTGATCGTTACGTTGACAAAATTGCA

GCTGGCGTTTTCCACAACTCCCTGCTGCCGGACACCGTTCACAGCCCGT

CTTACACTGTTGAAAAGCTGCTGGAATCGTTCCCGGACTGGCGTGACAC

AGAATATTTCACGTTCACCAACATCACTGGCGAAACCATCACTACCATG

AAACTGGGTTTCGTTCTGCTGCGTGAAAACCTGTTCACCAAATGCACTG

ATGGCGAATATGAACTGGCAAAAATGGTTATGCGCAAGGGCTCTCTGTT

CCAAAACGTTCTGGCTCAGCGTCCGAAGTTCACTGAAAAAGGCTACGGC

TCTATCAAGAAAGTTTATATTTGGACCGATCAAGACAAAATATTCCTGC

CGGACTTCCAACGCTGGCAAATTGCAAACTACAAACCGGACAAGGTTTA
```

-continued
```
TCAGGTTCAAGGCGGCGATCACAAGCTGCAGCTGACAAAAACTGAAGAA

GTAGCTCACATTCTGCAAGAAGTTGCTGATGCATACGCTTAA
```

Mutated Cyanohydrin Lyase with High Activity

The inventors of the present invention have developed a specific high-throughput screening method based on the reported cassava-derived S-cyanohydrin lyase MeHNL, and directed evolution has been carried out accordingly. Cyanohydrin lyase sequence with higher enzyme activity was obtained by further screening. The mutant enzyme was prepared by high-density fermentation of *E. coli*, and its catalytic performance and stereoselectivity were determined. It was found that the mutant enzymes have extremely high application value. The highest specific enzyme activity of the mutant enzyme on m-PBAld is more than 10 times of that of the wild type, and the ee value is as high as about 99%, which is higher than that of all the reported S-cyanohydrin lyases. The enzymic catalytic reaction is shown in the following formula:

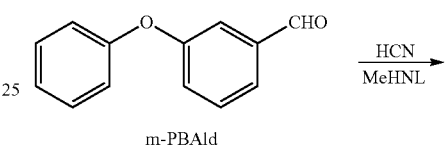

m-PBAld

-continued

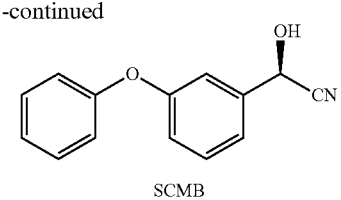

SCMB

Preferably, the conditions of catalytic reactions are as follow:

Enzyme activity assay: 1 U of enzyme activity is defined as the amount of enzyme required to catalyze the production of 1 μmol ether aldehyde per minute.

The enzyme activity assay was carried out by referring to the method reported by Selmar (Analytical Biochemistry 166 (1987), 208-211), with 10 mM m-phenoxybenzonitrile, 20 uL methanol, 20 mM citrate buffer (pH 5.0), and 10 uL enzyme solution. The above reaction solution was incubated at 25° C., and the change in absorbance at OD 310 nm was measured within 1-5 min. The curve of time (min) and absorbance change was drawn. The slope of the curve of the experimental group was set to ΔK, and the slope of the control group was zero. Under the same condition and without adding any enzyme solution, the change in absorbance at 310 nm wavelength, in 25° C., was recorded as a control group. The control group should not have a change in absorbance.

The slope of concentration standard curve of m-oxybenzaldehyde was K. The enzyme activity was calculated according to the formula:

$$\frac{\Delta K}{K} \times \frac{1}{1000} \times 1000 \times 100 \times \text{Dilution times}$$

Vector and Host Cell

The present invention also provides a vector comprising the optimized cyanohydrin lyase gene of the present invention, and a host cell containing the vector.

In a preferred embodiment of the invention, the vector has the ability to be expressed in *E. coli*, more preferably in *E. coli* BL21 (DE3) strain.

The optimized cyanohydrin lyase gene sequences of the invention can be obtained by conventional methods that can be used by one of ordinary skill in the art, such as fully artificial synthesis or PCR synthesis. A preferred method of synthesis is the asymmetric PCR method. The asymmetric PCR method uses a pair of primers with unequal amounts, and a large amount of single-stranded DNA (ssDNA) is produced by PCR amplification. The pair of primers are called unrestricted primer and restricted primer, respectively, and the ratio is generally 50-100:1. In the first 10-15 cycles of the PCR reaction, the amplified product is mainly double-stranded DNA. But when the restricted primer (low concentration primer) is consumed, the PCR guided by the unrestricted primer (high concentration primer) will produce a large amount of single-stranded DNA. The primers for PCR can be appropriately selected according to the sequence information of the present invention disclosed herein, and can be synthesized by a conventional method. The amplified DNA/RNA fragment can be isolated and purified by conventional methods such as gel electrophoresis.

The polynucleotide sequence of the present invention can express or produce a target protein by conventional recombinant DNA technology, comprising the steps of:

(1) transforming or transducing a suitable host cell, preferably an *E. coli* cell, with a polynucleotide (or variant) encoding the protein of the present invention, or with a recombinant expression vector containing the polynucleotide;

(2) culturing the host cell in a suitable medium;

(3) isolating and purifying the protein from the culture medium or cell.

Methods well known to the skilled in the art can be used to construct the expression vector, which contains the DNA sequence coding the protein of the invention and suitable transcription/translation control signals. Preferred commercially available vector is: pET28. These methods comprise DNA recombinant technology in vitro, DNA synthesis technology, recombinant technology in vivo, and the like. The DNA sequence can be operably linked to an appropriate promoter in an expression vector to direct mRNA synthesis. The expression vector also comprises a ribosome binding site for translation initiation and a transcription terminator. Furthermore, the expression vector preferably comprises one or more selectable marker genes to provide phenotypic traits for selection of transformed host cells.

The present invention also provides a recombinant vector comprising the optimized MeHNL DNA sequence of the present invention. In a preferred embodiment, the recombinant vector comprises a multiple cloning site or at least one restriction site downstream of the promoter. When a target gene needs to be expressed, the target gene can be ligated into a suitable multiple cloning site or a restriction site, thereby operably linking the target gene to the promoter.

In another preferred embodiment, the recombinant vector comprises: a promoter, a target gene, and a terminator in the 5' to 3' direction. If needed, the recombinant vector can also include the following elements: a protein purification tag; a 3' polynucleotide signal; a non-translated nucleic acid sequence; a transport and targeting nucleic acid sequence; a selectable marker (antibiotic resistance gene, fluorescent protein, etc.); an enhancer; or an operator.

Methods for preparing recombinant vectors are well known to the skilled in the art. The expression vector can be a bacterial plasmid, a phage, a yeast plasmid, a virus of plant cell, a virus of mammalian cell or other vectors. In all, any plasmid and vector can be employed as long as it is capable of replicating and is stable in the host.

The skilled in the art can construct the vector containing the promoter and/or target gene sequence of the present invention using well-known methods. These methods comprise DNA recombinant technology in vitro, DNA synthesis technology, recombinant technology in vivo, and the like.

The expression vector of the present invention can be used to transform an appropriate host cell such that the host transcribes the target RNA or expresses the target protein. The host cell can be a prokaryotic cell such as *Escherichia coli*, *Corynebacterium glutamicum*, *Brevibacterium flavum*, *Streptomyces*, *Agrobacterium*; or a lower eukaryotic cell, such as a yeast cell; or a higher eukaryotic cell, such as a plant cell. It will be apparent to the skilled in the art how to select an appropriate vector and host cell. Transformation of host cells with recombinant DNA can be carried out using conventional techniques well known to the skilled in the art. When the host is a prokaryote (such as *E. coli*), it can be treated with the $CaCl_2$ method or electroporation method. When the host is a eukaryote, the following DNA transfection methods can be used: calcium phosphate coprecipitation method, conventional mechanical method (such as microinjection, electroporation, liposome packaging, etc.). Transformation of plant can be carried out using *Agrobacterium* transformation or gene gun transformation or other methods, such as leaf disc method, immature embryo transformation method, flower bud soaking method and the like. The transformed plant cells, tissues or organs can be regenerated into plants using conventional method to obtain transgenic plants.

The term "operably linked" means that a target gene intended for transcriptional expression is linked to its control sequence for expression in a manner conventional in the art.

Culture of Engineering Bacteria and Fermentation Production of Target Protein

After obtained, the engineered cell can be cultured under suitable conditions to express the protein encoded by the gene sequence of the present invention. Depending on the difference of host cells, the medium used in the culture may be selected from various conventional mediums, and the host cells were cultured under conditions suitable for growth. After the host cells having grown to an appropriate cell density, the selected promoter is induced by a suitable method (such as temperature conversion or chemical induction) and the cells are cultured for a further period of time.

In the present invention, conventional fermentation conditions can be employed. Representative conditions include (but are not limited to):

(a) in terms of temperature, the fermentation and induction temperature of cyanohydrin lyase is maintained at 25-37° C.;

(B) in terms of pH during the induction period, the pH of the induction period is controlled at 3-9;

(C) in terms of dissolved oxygen (DO), the DO is controlled at 10-90%, and can be maintained by the passage of the oxygen/air mixture;

(d) in terms of additional medium, the type of additional medium should include carbon source such as glycerin, methanol, glucose, etc., which can be fed separately or by mix;

(e) in terms of IPTG concentration during the induction period, conventional induced concentration can be used in the present invention, and usually the IPTG concentration is controlled at 0.1-1.5 mM;

(f) in terms of induction time, there is no particular limitation, and it is usually 2 to 20 hours, preferably 5 to 15 hours.

The target protein cyanohydrin lyase of the present invention exists in the cells of *Escherichia coli*. The host cells are collected by a centrifuge. Then the host cells are disrupted by high pressure, machine power, enzymatic digestion of cell or other cell disruption methods to release the recombinant protein, and a preferred method is high pressure method. The host cell lysate can be preliminary purified by methods such as flocculation, salting out, ultrafiltration, etc., followed by purification such as chromatography, ultrafiltration, etc. The protein can also be purified directly by chromatography.

Chromatography technology comprises cation exchange chromatography, anion exchange chromatography, gel filtration chromatography, hydrophobic chromatography, affinity chromatography and the like. Commonly used chromatographic method comprises:

1. Anion Exchange Chromatography:

Anion exchange chromatography media comprise, but are not limited to, Q-Sepharose, DEAE-Sepharose. If the salt concentration of the fermented sample is too high to affect the binding to the ion exchange media, the salt concentration needs to be reduced before ion exchange chromatography. The balance buffer of sample can be replaced by dilution, ultrafiltration, dialysis and gel filtration chromatography, etc., until it is similar to the corresponding equilibrium liquid system of ion exchange column. Then the sample is loaded for gradient elution of salt concentration or pH.

2. Hydrophobic Chromatography:

Hydrophobic chromatography media comprise, but are not limited to: Phenyl-Sepharose, Butyl-Sepharose, Octyle-Sepharose. The salt concentration of sample is increased by adding NaCl, $(NH_4)_2SO_4$ and the like. Then the sample is loaded and eluted by reducing the salt concentration. Impurity protein with a great difference in hydrophobicity is removed by hydrophobic chromatography.

3. Gel Filtration Chromatography

Hydrophobic chromatography media comprise, but are not limited to, Sephacryl, Superdex, Sephadex. By gel filtration chromatography, the buffer system is replaced or the sample is further purified.

4. Affinity Chromatography

Affinity chromatography media comprise, but are not limited to, HiTrap™ Heparin HP Columns.

5. Membrane Filtration

The ultrafiltration media comprise organic membranes (such as polysulfone membranes), inorganic membranes (such as ceramic membranes, and metal membranes). Purification and concentration can be achieved by membrane filtration.

Preparation of Composition of Enzyme Preparation

The present invention also provides a composition of enzyme preparation comprising the cyanohydrin lyase of the present invention.

The composition of enzyme preparation of the present invention may further comprise: citric acid, tartaric acid, and/or boric acid.

Method for Preparing S-Cyanohydrin

The present invention also provides a method for preparing S-cyanohydrin, comprising the steps of:

(1) contacting the mutated cyanohydrin lyase of the present invention with a reaction substrate to carry out a catalytic reaction, thereby producing the S-cyanohydrin;

(2) isolating and purifying the S-cyanohydrin product.

In a preferred embodiment of the invention, in step (1), the reaction substrate is m-phenoxybenzaldehyde, and acetone cyanohydrin (or hydrogen cyanide (or sodium cyanide/cyanide)).

In a preferred embodiment of the invention, in step (1), the temperature of the catalytic reaction is 0-20° C.

The main advantages of the invention are:

(1) the catalytic activity of the mutated S cyanohydrin lyase according to the present invention is significantly improved compared to that of the wild type, and the catalytic activity of some mutants is even more than 10 times of that of the wild type;

(2) the mutated S cyanohydrin lyase according to the present invention can be expressed in large quantities in engineered *Escherichia coli*, and thus reducing the preparation cost.

(3) the mutated S cyanohydrin lyase according to the present invention can be expressed at high temperature (about 25-37° C.), which greatly reduces the production cost and simplifies the fermentation process, while the lyase expressed at high temperature by the wild-type and some mutants has no activity or very low activity The invention is further illustrated by the following specific examples. It is to be understood that these examples are for illustrative purposes only and are not intended to limit the scope of the invention. The experimental methods in the following examples which do not specify the specific conditions are usually performed under conventional conditions, for example, conditions described in Sambrook. J et al., Molecular Cloning-A Laboratory Manual (translated by Huang Peitang et al., Beijing: Science Press, 2002.), or in accordance with the conditions recommended by the manufacturer. Percentages and parts are by weight unless otherwise stated. The experimental materials and reagents used in the following examples are commercially available unless otherwise specified.

Example 1: Construction of a Mutant Library

Taking the H103 mutation as an example, the construction steps of the mutant library were as follows:

Site-saturated mutant was performed on H103 and primers were designed.

```
H103-f:
                                    (SEQ ID NO. 3)
5'-GCAGCTGGCGTTTTCNNNAACTCCCTGCTGCCG-3'

H103-r:
                                    (SEQ ID NO. 4)
5'-CGGCAGCAGGGAGTTNNNGAAAACGCCAGCTGC-3'
```

The target band was amplified by PCR using plasmid pET21a-meHNL as the template. The procedure is as follows:

| | | |
|---|---|---|
| 95° C. | 5 min | |
| 95° C. | 30 s | |
| 50° C. | 30 s | 30 cycles |
| 72° C. | 5 min | |
| 72° C. | 10 min | |
| 12° C. | ∞ | |

PCR product was digested with Dpn I at 37° C. for 2 hours. After the reaction, the digestive solution was transformed into competent cell *E. coli* BL21 (DE3). Then the strains were coated on LB medium that containing 100 ug/mL ampicillin, and cultured overnight at 37° C. to obtain a mutant library.

The construction of mutant library of other sites was performed in the same manner as above. Primer sequences designed for the construction of mutant library of other sites are shown in the following table:

TABLE 1

| Number | Mutation site and primer name | Primer sequence | SEQ ID NO. |
|---|---|---|---|
| 1 | H103-f | GCAGCTGGCGTTTTCNNNAACTCCCTGCTGCCG | 3 |
| 2 | H103-r | CGGCAGCAGGGAGTTNNNGAAAACGCCAGCTGC | 4 |
| 3 | W128-f | GAATCGTTCCCGGACNNNCGTGACACAGAATAT | 5 |
| 4 | W128-r | ATATTCTGTGTCACGNNNGTCCGGGAACGATTC | 6 |
| 5 | V2-f | GGAGATATACATATGNNNACTGCACACTTCGTT | 7 |
| 6 | V2-r | AACGAAGTGTGCAGTNNNCATATGTATATCTCC | 8 |
| 7 | L36-f | CACAAAGTTACTGCANNNGACATGGCAGCCAGT | 9 |
| 8 | L36-r | ACTGGCTGCCATGTCNNNTGCAGTAACTTTGTG | 10 |
| 9 | C81-f | CATTGTTGGTGAAAGCNNNGCAGGCCTGAACATTG | 11 |
| 10 | C81-r | CAATGTTCAGGCCTGCNNNGCTTTCACCAACAATG | 12 |
| 11 | V94-f | GCTGCTGATCGTTACNNNGACAAAATTGCAGCT | 13 |
| 12 | V94-r | AGCTGCAATTTTGTCNNNGTAACGATCAGCAGC | 14 |
| 13 | L121-f | CTTACACTGTTGAAAAGNNNCTGGAATCGTTCCCG | 15 |
| 14 | L121-r | CGGGAACGATTCCAGNNNCTTTTCAACAGTGTAAG | 16 |
| 15 | L122-f | ACTGTTGAAAAGCTGNNNGAATCGTTCCCGGAC | 17 |
| 16 | L122-r | GTCCGGGAACGATTCNNNCAGCTTTTCAACAGT | 18 |
| 17 | F125-f | AAGCTGCTGGAATCGNNNCCGGACTGGCGTGAC | 19 |
| 18 | F125-r | GTCACGCCAGTCCGGNNNCGATTCCAGCAGCTT | 20 |
| 19 | D127-f | CTGGAATCGTTCCCGNNNGCACGTGACACAGAA | 21 |
| 20 | D127-r | TTCTGTGTCACGTGCNNNCGGGAACGATTCCAG | 22 |
| 21 | R129-f | TCGTTCCCGGACGCANNNGACACAGAATATTTC | 23 |
| 22 | R129-r | GAAATATTCTGTGTCNNNTGCGTCCGGGAACGA | 24 |
| 23 | T140-f | ACGTTCACCAACATCNNNGGCGAAACCATCACT | 25 |
| 24 | T140-r | AGTGATGGTTTCGCCNNNGATGTTGGTGAACGT | 26 |
| 25 | M147-f | GAAACCATCACTACCNNNAAACTGGGTTTCGTT | 27 |
| 26 | M147-r | AACGAAACCCAGTTTNNNGGTAGTGATGGTTTC | 28 |
| 27 | L149-f | CATCACTACCATGAAANNNGGTTTCGTTCTGCTGC | 29 |
| 28 | L149-r | GCAGCAGAACGAAACCNNNTTTCATGGTAGTGATG | 30 |
| 29 | G165-f | ACCAAATGCACTGATNNNGAATATGAACTGGCA | 31 |
| 30 | G165-r | TGCCAGTTCATATTCNNNATCAGTGCATTTGGT | 32 |
| 31 | V173-f | GAACTGGCAAAAATGNNNATGCGCAAGGGCTCT | 33 |

TABLE 1-continued

| Number | Mutation site and primer name | Primer sequence | SEQ ID NO. |
|---|---|---|---|
| 32 | V173-r | AGAGCCCTTGCGCATNNNCATTTTTGCCAGTTC | 34 |
| 33 | K176-f | CAAAAATGGTTATGCGCNNNGGCTCTCTGTTCCAAAAC | 35 |
| 34 | K176-r | GTTTTGGAACAGAGAGCCNNNGCGCATAACCATTTTTG | 36 |
| 35 | K199-f | GGCTACGGCTCTATCNNNAAAGTTTATATTTGG | 37 |
| 36 | K199-r | CCAAATATAAACTTTNNNGATAGAGCCGTAGCC | 38 |
| 37 | K209-f | TGGACCGATCAAGACNNNATATTCCTGCCGGAC | 39 |
| 38 | K209-r | GTCCGGCAGGAATATNNNGTCTTGATCGGTCCA | 40 |
| 39 | Q216-f | TTCCTGCCGGACTTCNNNCGCTGGCAAATTGCA | 41 |
| 40 | Q216-r | TGCAATTTGCCAGCGNNNGAAGTCCGGCAGGAA | 42 |
| 41 | K224-f | CAAATTGCAAACTACNNNCCGGACAAGGTTTATC | 43 |
| 42 | K224-r | GATAAACCTTGTCCGGNNNGTAGTTTGCAATTTG | 44 |

Wherein, N in the sequences of the present application represents A, T, G or C.

Example 2: High Throughput Screening

Screening was according to the following experimental steps:

1. Clones were selected and inoculating on a 96-well plate 1 (500 μL TB medium per well), and cultured overnight at 30° C.;
2. Media were transferred a new 96-well plate 2 (800 μL TB medium per well, 0.15 mM IPTG), wherein 100 μL medium from 96-well plate 1 was inoculated to 96-well plate 2, and cultured overnight at 30° C.
3. The strain in 96-well plate 2 was collected, 100 μL BugBuster Protein Extraction Reagent (Novagen) was added. The mixture was treated for 30 min, and then centrifuged to obtain the supernatant.
4. The enzyme solution was diluted to a reasonable multiple.
5. The elisa plate was prepared with 200 μL reaction system containing 150 μL of 50 mM citrate buffer (containing 15% methanol), 5 μL of substrate SCMB (0.05 g/mL dissolved in methanol), 5 μL of enzyme solution, and the mixture was reacted for 2 min. Then 10 μL Solution I (100 mM N-chlorosuccinimide) was immediately added and reacted for 2 min. Then 30 μL Solution II (65 mM isonicotinic acid and 125 mM barbituric acid, which were dissolved in 0.2 M NaOH) was added. The reading was taken at a wavelength of 600 nm after 20 min.
6. Using the wild type as the reference system, the clone with strongest absorbance at 600 nm was selected as the most positive clone, and its enzyme activity and specific enzyme activity were analyzed.

Enzyme activity assay: 1 U of enzyme activity was defined as the amount of enzyme required to catalyze the production of 1 μmol ether aldehyde per minute.

The enzyme activity assay was carried out by referring to the method reported by Selmar (Analytical Biochemistry 166 (1987), 208-211), with 10 mM m-phenoxybenzonitrile, 20 uL methanol, 20 mM citrate buffer (pH 5.0), and 10 uL enzyme solution. The above reaction solution was incubated at 25° C., and the change in absorbance at OD 310 nm was measured within 1-5 min. The curve of time (min) and absorbance change was drawn. The slope of the curve of the experimental group was set to ΔK, and the slope of the control group was zero. Under the same condition and without adding any enzyme solution, the change in absorbance at 310 nm wavelength, in 25° C., was recorded as a control group. The control group should not have a change in absorbance.

The slope of concentration standard curve of m-oxybenzaldehyde was K. The enzyme activity was calculated according to the formula:

$$\frac{\Delta K}{K} \times \frac{1}{1000} \times 1000 \times 100 \times \text{Dilution times}$$

Determination of protein concentration: The absorption at OD280 is determined according to the standard procedure of Nanodrop2000, and the concentration c (mg/mL) of protein in the lysate is obtained;

Calculation of specific enzyme activity: specific enzyme activity (U/mg)=enzyme activity/protein concentration.

Example 3: High-Density Fermentation

The deoxyribonucleic acid sequence encoding the mutant enzyme was synthesized, and ligated into the NdeI and XhoI sites of the pET28a vector (purchased from Novagen) to obtain an E. coli plasmid pET28-MeHNL6 containing a T7 promoter. The plasmid was transformed into E. coli BL21 (DE3) (purchased from Invitrogene), and the corresponding strain was obtained on a Kana-resistant plate. Then the strain was inoculated into LB medium and cultured overnight at 37° C. The strain was preserved with 20% glycerol.

The strain was inoculated into a 1 L shake flask containing 200 mL LB medium, and cultured at 37° C., 180-220 rpm for 10-16 h. The above cultured seeds were inoculated into a 3 L upper tank fermentation medium (M9) (glucose 4 g/L, disodium hydrogen phosphate 12.8 g/L, potassium dihydrogen phosphate 3 g/L, ammonium chloride 1 g/L, sodium sulfate 0.5 g/L, calcium chloride 0.0152 g/L, magnesium chloride hexahydrate 0.41 g/L) at a ratio of 10% (v/v). The mixture was incubated at 25-35° C., 300-800 rpm, with 2-6 L/min air flow. After 6-10 h of culture, IPTG was added for induction for 10-12 h, and a supplementary medium containing 60% glycerol was added at a rate of 5-20 mL/h until the end of the fermentation. Supplementary medium was added for several hours until the $OD_{600}$ reached 80-100. The fermentation was stopped and the strains were collected by 5 000 rpm centrifugation. The enzyme activity was measured after lysing the strains. Gel electrophoresis assay result was as expected.

Fermentation Preparation for Wild Type and Some of Mutants

It has been found that under high temperature fermentation (about 25-37° C.), the wild type (SEQ ID NO. 1) and some of mutants (such as mutant 2) expressed by the engineered bacteria have extremely low activity, and the wild type has substantially no activity.

Therefore, the fermentation method for wild type and some of mutants (such as mutant 2) is basically the same as above, except that the temperature is maintained at a low level (about 12-16° C.) during the fermentation.

Example 4: Purification of Enzyme

The enzyme obtained by fermentation can be purified using a method conventional in the art. The enzyme obtained by fermentation can also be purified by the following method, for example:

1 L fermentation broth which containing strains having wild-type sequence was centrifuged (4000 rpm) to obtain 50 g cells. The cells were resuspended in 20 mM sodium phosphate buffer (pH 5.5) in a ratio of 4 mL buffer per gram cells. The cells were crushed with a high-pressure homogenizer (with a pressure of 800-1000 bar). Polyacrylamide was added for flocculation (1-2‰), and the supernatant was collected after centrifugation at 4000 rpm. The supernatant was concentrated 8 times with an ultrafiltration membrane (with a protein concentration of 93 mg/mL) and the enzyme activity was 198 U/mL.

1 L fermentation broth which containing strains having sequence of mutant 9 was centrifuged (4000 rpm) to obtain 50 g cells. The cells were resuspended in 20 mM potassium citrate buffer (pH 5.5) in a ratio of 4 mL buffer per gram cells. The cells were crushed with a high-pressure homogenizer (with a pressure of 800-1000 bar). Polyacrylamide was added for flocculation (1-2‰), and the supernatant was collected after centrifugation at 4000 rpm. The supernatant was concentrated 5 times with an ultrafiltration membrane (with a protein concentration of 65 mg/mL) and the enzyme activity was 522 U/mL.

1 L fermentation broth which containing strains having sequence of mutant 27 was centrifuged (4000 rpm) to obtain 50 g cells. The cells were resuspended in 20 mM potassium phosphate buffer (pH 5.5) in a ratio of 4 mL buffer per gram cells. The cells were crushed with a high-pressure homogenizer (with a pressure of 800-1000 bar). Polyacrylamide was added for flocculation (1-2‰), and the supernatant was collected after centrifugation at 4000 rpm. The supernatant was concentrated 5 times with an ultrafiltration membrane (with a protein concentration of 69 mg/mL) and the enzyme activity was 687 U/mL.

1 L fermentation broth which containing strains having sequence of mutant 55 was centrifuged (4000 rpm) to obtain 50 g cells. The cells were resuspended in 50 mM sodium citrate buffer (pH 5.5) in a ratio of 4 mL buffer per gram cells. The cells were crushed with a high-pressure homogenizer (with a pressure of 800-1000 bar). Polyacrylamide was added for flocculation (1-2‰), and the supernatant was collected after centrifugation at 4000 rpm. The supernatant was concentrated 5 times with an ultrafiltration membrane (with a protein concentration of 62 mg/mL) and the enzyme activity was 958 U/mL.

1 L fermentation broth which containing strains having sequence of mutant 72 was centrifuged (4000 rpm) to obtain 50 g cells. The cells were resuspended in 20 mM sodium tartrate buffer (pH 5.0) in a ratio of 4 mL buffer per gram cells. The cells were crushed with a high-pressure homogenizer (with a pressure of 800-1000 bar). Polyethyleneimine was added for flocculation (1-2‰), and the supernatant was collected after centrifugation at 4000 rpm. The supernatant was concentrated 5 times with an ultrafiltration membrane (with a protein concentration of 75 mg/mL) and the enzyme activity was 1530 U/mL.

1 L fermentation broth which containing strains having sequence of mutant 113 was centrifuged (4000 rpm) to obtain 50 g cells. The cells were resuspended in 20 mM sodium citrate-20 mM sodium phosphate buffer (pH 5.0) in a ratio of 4 mL buffer per gram cells. The cells were crushed with a high-pressure homogenizer (with a pressure of 800-1000 bar). Polyethyleneimine was added for flocculation (1-2‰), and the supernatant was collected after centrifugation at 4000 rpm. The supernatant was concentrated 3 times with an ultrafiltration membrane (with a protein concentration of 64 mg/mL) and the enzyme activity was 1613 U/mL.

1 L fermentation broth which containing strains having sequence of mutant 135 was centrifuged (4000 rpm) to obtain 50 g cells. The cells were resuspended in 20 mM sodium citrate–20 mM sodium phosphate buffer (pH 5.2) in a ratio of 4 mL buffer per gram cells. The cells were crushed with a high-pressure homogenizer (with a pressure of 800-1000 bar). Polyethyleneimine was added for flocculation (1-2‰), and the supernatant was collected after centrifugation at 4000 rpm. The supernatant was concentrated 3 times with an ultrafiltration membrane (with a protein concentration of 55 mg/mL) and the enzyme activity was 1876 U/mL.

1 L fermentation broth which containing strains having sequence of mutant 149 was centrifuged (4000 rpm) to obtain 50 g cells. The cells were resuspended in 20 mM potassium phosphate buffer (pH 5.5) in a ratio of 4 mL buffer per gram cells. The cells were crushed with a high-pressure homogenizer (with a pressure of 800-1000 bar). Polyacrylamide was added for flocculation (1-2‰), and the supernatant was collected after centrifugation at 4000 rpm. The supernatant was concentrated 6 times with an ultrafiltration membrane (with a protein concentration of 56 mg/mL) and the enzyme activity was 680 U/mL.

The results of the specific enzyme activity are shown in FIG. 1.

The results of enzyme activity assay of the wild type and the selected mutant enzymes of the present invention are shown in Table 2.

TABLE 2

| Mutant enzyme number | Mutation site | Enzyme activity |
| --- | --- | --- |
| 1 | WT | * |
| 2 | H103M, W128A | * |
| 3 | L36A, H103L, W128A | ** |

TABLE 2-continued

| Mutant enzyme number | Mutation site | Enzyme activity |
|---|---|---|
| 4 | V94E, H103L, W128A | ** |
| 5 | L36C, H103L, W128A | ** |
| 6 | L36Y, H103L, W128A | ** |
| 9 | V94L, H103L, W128A | ** |
| 10 | L36Q, H103L, W128A | ** |
| 13 | C81Y, H103L, W128A | ** |
| 18 | V94Q, H103L, W128A | ** |
| 20 | V94H, H103L, W128A | ** |
| 21 | H103L, W128A, V173T | ** |
| 22 | C81Y, H103L, W128A | ** |
| 27 | C81V, H103L, W128A | ** |
| 29 | H103L, W128A, V173I | ** |
| 30 | V94T, H103L, W128A | ** |
| 31 | H103L, W128A, V173C | ** |
| 34 | H103L, W128A, I49A | ** |
| 35 | V94F, H103L, W128A | ** |
| 36 | H103L, W128A, V173A | ** |
| 37 | L36I, H103L, W128A | ** |
| 38 | H103L, W128A, V173S | ** |
| 39 | L36F, H103L, W128A | ** |
| 40 | H103S | ** |
| 41 | C81I, H103L, W128A | *** |
| 42 | V94A, H103L, W128A | *** |
| 43 | V2P, H103L, W128A | *** |
| 44 | V2W, H103L, W128A | *** |
| 45 | V2T, H103L, W128A | *** |
| 46 | V94S, H103L, W128A, K209R | *** |
| 47 | H103L, W128A, V173L, K209C | *** |
| 48 | V94R, H103L, W128A, K209C | *** |
| 49 | H103V | *** |
| 50 | H103L, W128A, G165T | *** |
| 51 | H103L, W128A, V173L, K209S | *** |
| 52 | V2H, H103L, W128A | *** |
| 53 | H103L, W128A, K224T | *** |
| 54 | V2D, H103L, W128A | *** |
| 55 | V94G, H103L, W128A | *** |
| 56 | V2P, C81A H103L, W128A, L149C | *** |
| 57 | V2S, H103L, W128A | *** |
| 58 | H103L, W128A, K224A | *** |
| 59 | V2Q, H103L, W128A | *** |
| 60 | H103L, W128A, K199P, K176P | *** |
| 61 | V2R, H103L, W128A | *** |
| 62 | V94R, H103L, W128A, V173L | *** |
| 63 | H103I | *** |
| 64 | H103L, W128A, K199P | *** |
| 65 | H103L, W128A, K176P | *** |
| 66 | V94C, H103L, W128A | *** |
| 67 | H103L, W128A, K224N | *** |
| 68 | H103L, W128A, K224D | *** |
| 69 | V94S, H103L, W128A, V173L | **** |
| 70 | H103L, W128A, K199P, K224P | **** |
| 71 | V2C, H103L, W128A | **** |
| 72 | H103L, W128A | **** |
| 73 | H103L, W128A, K224P | **** |
| 74 | H103L, W128A, V173L | **** |
| 75 | H103L, W128A, K224H | **** |
| 76 | H103L, W128A, K224I | **** |
| 77 | H103L, W128A, K224S | **** |
| 78 | H103L, W128A, K224V | **** |
| 79 | H103L, W128A, G165S | **** |
| 80 | H103L, W128A, K176P, K224P | **** |
| 81 | H103C | **** |
| 82 | H103L, W128A, V173Q | **** |
| 83 | H103L, W128A, K224E | **** |
| 84 | V94S, H103L, W128A, K209C | **** |
| 85 | H103L, W128A, K224P | **** |
| 86 | H103L, W128A, T140R | ***** |
| 87 | H103L | ***** |
| 88 | H103L, W128A, T140S | ***** |
| 89 | H103L, W128A, T140W | ***** |
| 90 | H103L, W128A, T140D | ***** |
| 91 | V94S, H103L, W128A, G165D | ***** |
| 92 | H103L, W128A, T140I | ***** |
| 93 | H103L, W128A, T140K | ***** |
| 94 | H103L, W128A, G165P | ***** |
| 95 | H103L, W128A, T140G | ***** |
| 96 | H103L, W128A, T140H | ***** |
| 97 | V94R, H103L, W128A | ***** |
| 98 | H103L, W128A, K209F | ***** |
| 99 | H103L, W128A, G165D | ***** |
| 100 | V94R, H103L, W128A, K209R | ***** |
| 101 | V94R, H103L, W128A, G165D | ***** |
| 102 | V94S, H103L, W128A | ***** |
| 103 | H103L, W128A, K209L | ***** |
| 104 | C81A, H103L, W128A | ***** |
| 105 | H103L, W128A, K209M | ***** |
| 106 | H103L, W128A, K209G | ***** |
| 107 | H103L, W128A, K209A | ***** |
| 108 | H103L, W128A, K209S | ***** |
| 109 | H103L, W128A, K209C | ***** |
| 110 | C81A, H103L, W128A, K224P | ***** |
| 111 | C81A, H103L, W128A | ***** |
| 112 | H103L, W128A, K209R | ***** |
| 113 | V2I, H103L, W128A | ***** |
| 114 | C81A, H103L, W128A, K176P | ***** |
| 115 | V2A, C81A, H103L, W128A, L149C | ***** |
| 116 | L36A, H103L, W128A | ***** |
| 117 | V2G, C81A, H103L, W128A | ****** |
| 118 | V2L, C81A, H103L, W128A | ****** |
| 119 | V2P, C81A, H103L, W128A | ****** |
| 120 | V2H, C81A, H103L, W128A | ****** |
| 121 | V2R, C81A, H103L, W128A | ****** |
| 122 | V2M, C81A, H103L, W128A | ****** |
| 123 | V2S, C81A, H103L, W128A | ****** |
| 124 | V2C, C81A, H103L, W128A | ****** |
| 125 | V2W, C81A, H103L, W128A | ****** |
| 126 | V2T, C81A, H103L, W128A | ****** |
| 127 | V2Q, C81A, H103L, W128A | ****** |
| 128 | V2A, C81A, H103L, W128A | ****** |
| 129 | C81A, H103L, W128A, L149P | ****** |
| 130 | C81A, H103L, W128A, L149I | ****** |
| 131 | C81A, H103L, W128A, L149C | ****** |
| 132 | C81A, V94P, H103L, W128A, K176P | ****** |
| 133 | C81A, 94R, H103L, W128A, L149P | ****** |
| 134 | C81A, 94K, H103L, W128A, L149P | ****** |
| 135 | V2P, C81A, H103L, W128A, L149C | ****** |
| 136 | H103I, W128A | **** |
| 137 | H103V, W128A | **** |
| 138 | H103C, W128A | **** |
| 139 | H103S, W128A | **** |
| 140 | H103I, W128Y | ** |
| 141 | H103L, W128N | *** |
| 142 | H103L, W128G | *** |
| 143 | H103L, W128Y | *** |
| 144 | H103I, W128N | *** |
| 145 | H103I, W128G | *** |
| 146 | H103C, W128V | *** |
| 147 | H103C, W128G | *** |
| 148 | H103C, W128Y | *** |
| 149 | H103M, W128L | *** |

Note:
* represents a specific activity between 0-3.0 U/mg;
** represents a specific activity between 3.0-10.0 U/mg;
*** represents a specific activity between 10.0-18.0 U/mg;
**** represents a specific activity between 18.0-26.0 U/mg;
***** represents a specific activity between 26.0-34.0 U/mg;
****** represents a specific activity of >34.0 U/mg.

Example 5: Biocatalytic Transformation of S-Cyanohydrin and Detection Method

The biocatalytic transformation of S-cyanohydrin was carried out by adding 20 mL of cyanohydrin lyase, 10 mL of aldehyde m-PBAld, 20 mL of methyl tert-butyl ether, and 3 g of HCN to a 100 mL reaction flask, and stirring and reacting at 15° C.

The detection method was as follows:

The reaction was monitored by high performance liquid chromatography (HPLC). Water and acetonitrile (45:55) were used as mobile phase. The chromatographic column was ODS-18 reversed phase column. Shimadzu LC-15C high performance liquid chromatography was used. UV absorption was detected at 210 nm. The reaction system was diluted with water and acetonitrile (45:55), then injected and detected after centrifugation and filtration with a nylon membrane. In the preferred reaction system of the present invention, the reaction progress detecting by HPLC was as follow: after 1 hour of reaction, m-phenoxybenzaldehyde was detected at 17.3 min and S-configuration cyanohydrin was detected at 17.5 min.

The chiral purity was analyzed by Agilent 1260 liquid chromatography under the conditions of Chiralpak AD-H column, n-hexane:ethanol (0.1% DEA)=90:10, 0.8 mL/min, and the detection wavelength was 220 nm. After comparison, the product of S-configuration prepared by the invention is identical to the target standard substance (purchased from Jiangxi Keyuan Biopharmaceutical Co., Ltd.).

Typical catalytic reactions and detection results involved in the present invention are exemplified as follows:

1. Wild Type 20 mL of cyanohydrin lyase (50 mg/mL, wild type, SEQ ID NO. 1), 10 mL of aldehyde m-PBAld, 20 mL of methyl tert-butyl ether, and 3 g of HCN were added to a 100 mL reaction flask, then stirred and reacted at 15° C. for 2 hours. The reaction progress was sampled and detected every 30 minutes. The ee value was 95.9%.

2. Mutant 9

20 mL of concentrated cyanohydrin lyase (50 mg/mL), 10 mL of aldehyde m-PBAld, 20 mL of methyl tert-butyl ether, and 3 g of HCN were added to a 100 mL reaction flask, then stirred and reacted at 15° C. for 2 hours. The reaction progress was sampled and detected every 30 minutes. The ee value was 99.5%.

3. Mutant 27

20 mL of concentrated cyanohydrin lyase (50 mg/mL), 10 mL of aldehyde m-PBAld, 20 mL of methyl tert-butyl ether, and 3 g of HCN were added to a 100 mL reaction flask, then stirred and reacted at 15° C. for 2 hours. The reaction progress was sampled and detected every 30 minutes. The ee value was 97.7%.

4. Mutant 55

20 mL of concentrated cyanohydrin lyase (50 mg/mL), 10 mL of aldehyde m-PBAld, 20 mL of methyl tert-butyl ether, and 4.5 g of acetone cyanohydrin were added to a 100 mL reaction flask, then stirred and reacted at 15° C. for 2 hours. The reaction progress was sampled and detected every 30 minutes. The ee value was 98.1%.

5. Mutant 72

20 mL of concentrated cyanohydrin lyase (50 mg/mL), 10 mL of aldehyde m-PBAld, 20 mL of methyl tert-butyl ether, 5 g of NaCN, and 1 mL of concentrated sulfuric acid were added to a 100 mL reaction flask, then stirred and reacted at 15° C. for 2 hours. The reaction progress was sampled and detected every 30 minutes. The ee value was 97.8%.

6. Mutant 113

20 mL of concentrated cyanohydrin lyase (50 mg/mL, mutant SEQ ID NO. 113), 10 mL of aldehyde m-PBAld, 20 mL of methyl tert-butyl ether, 5 g of KCN, and 1 mL of concentrated sulfuric acid were added to a 100 mL reaction flask, then stirred and reacted at 15° C. for 2 hours. The reaction progress was sampled and detected every 30 minutes. The ee value was 99.1%.

7. Mutant 135

20 mL of concentrated cyanohydrin lyase (50 mg/mL, mutant SEQ ID NO. 135), 10 mL of aldehyde m-PBAld, 20 mL of methyl tert-butyl ether, 3 g of HCN, and 1 mL of concentrated sulfuric acid were added to a 100 mL reaction flask, then stirred and reacted at 15° C. for 2 hours. The reaction progress was sampled and detected every 30 minutes. The ee value was 98.9%.

8. Mutant 149

20 mL of concentrated cyanohydrin lyase (50 mg/mL), 10 mL of aldehyde m-PBAld, 20 mL of methyl tert-butyl ether, and 3 g of HCN were added to a 100 mL reaction flask, then stirred and reacted at 15° C. for 2 hours. The reaction progress was sampled and detected every 30 minutes. The ee value was 99.1%.

Figure 2:
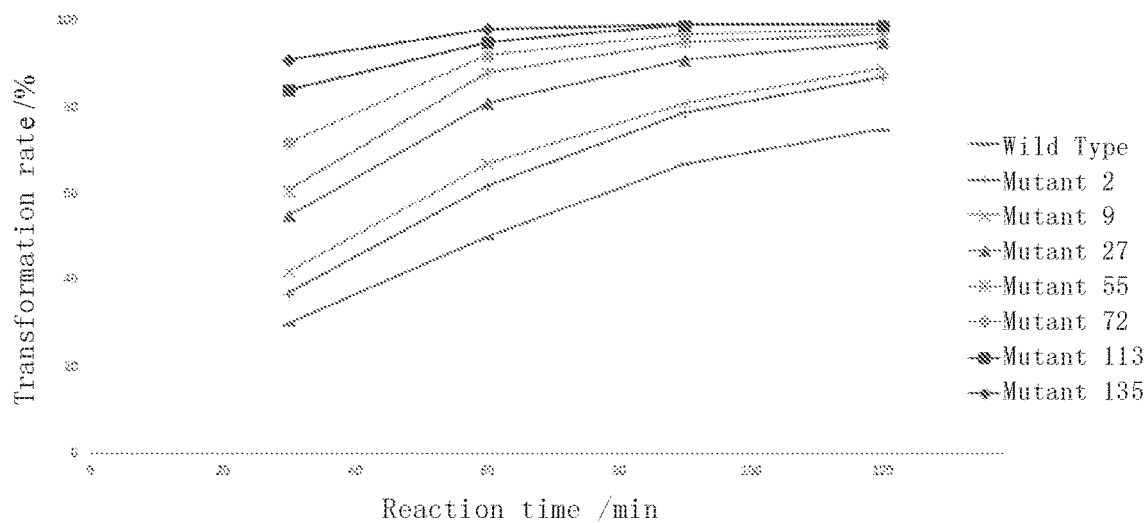
FIG. 2 shows the results of catalytic reaction monitoring of wild type and some of the typical mutants of the invention.

The monitoring results of the catalytic reaction are shown in FIG. 2.

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

The invention claimed is:

1. A mutated S-cyanohydrin lyase, which is mutated at two or more sites comprising amino acid residue of position 103 and amino acid residue of position 128 of SEQ ID NO. 1, wherein the amino acid residue of position 103 is mutated from H to L, I, V, C, S or M, the amino acid residue of position 128 is mutated from W to A, N, L, V, G or Y, and the amino acid sequence of the mutated S-cyanohydrin lyase has at least 80% homology to SEQ ID NO. 1.

2. The mutated S-cyanohydrin lyase of claim 1, wherein the amino acid residue of position 103 is mutated from H to L.

3. The mutated S-cyanohydrin lyase of claim 1, wherein the amino acid residue of position 128 is mutated from W to A.

4. A host cell expressing the mutated S-cyanohydrin lyase of claim 1.

5. An enzyme preparation comprising the mutated S-cyanohydrin lyase of claim 1.

6. A method for preparing S-cyanohydrin comprising the steps of:
(i) contacting the mutated cyanohydrin lyase of claim 1 or an enzyme preparation comprising the mutated S-cyanohydrin lyase with a reaction substrate to carry out a catalytic reaction, thereby producing the S-cyanohydrin;
(ii) isolating and purifying the S-cyanohydrin product.

7. The mutated S-cyanohydrin lyase of claim 1, wherein the mutated S-cyanohydrin lyase is mutated at one or more sites selected from the group consist of: amino acid residue of position 2, amino acid residue of position 81, amino acid residue of position 149, amino acid residue of position 176, amino acid residue of position 209, amino acid residue of position 94, amino acid residue of position 165, amino acid residue of position 140, amino acid residue of position 224, amino acid residue of position 173, and amino acid residue of position 36 of SEQ ID NO. 1.

8. The mutated S-cyanohydrin lyase of claim 7, wherein the amino acid residue of position 2 is mutated from V to P, L, D, I, G, H, R, M, S, C, W, T, Q, or A; and/or
the amino acid residue of position 81 is mutated from C to A, V or I; and/or
the amino acid residue of position 149 is mutated from L to I, C, A or P; and/or
the amino acid residue of position 94 is mutated from V to P, R, S, K; and/or
the amino acid residue of position 176 is mutated from K to P.

* * * * *

SEQUENCE LISTING

```
<160> NUMBER OF SEQ ID NOS: 46

<210> SEQ ID NO 1
<211> LENGTH: 258
<212> TYPE: PRT
<213> ORGANISM: Artificial Sequence
<220> FEATURE:
<223> OTHER INFORMATION: cassava cyanohydrin lyase

<400> SEQUENCE: 1

Met Val Thr Ala His Phe Val Leu Ile His Thr Ile Cys His Gly Ala
1               5                   10                  15

Trp Ile Trp His Lys Leu Lys Pro Ala Leu Glu Arg Ala Gly His Lys
            20                  25                  30

Val Thr Ala Leu Asp Met Ala Ala Ser Gly Ile Asp Pro Arg Gln Ile
        35                  40                  45

Glu Gln Ile Asn Ser Phe Asp Glu Tyr Ser Glu Pro Leu Leu Thr Phe
    50                  55                  60
```

| | | | | | | | | | | | | | | |
|---|---|---|---|---|---|---|---|---|---|---|---|---|---|---|
Leu | Glu | Lys | Leu | Pro | Gln | Gly | Glu | Lys | Val | Ile | Val | Gly | Glu | Ser
65 | | | | 70 | | | | 75 | | | | | | 80

Cys Ala Gly Leu Asn Ile Ala Ile Ala Ala Asp Arg Tyr Val Asp Lys
               85                     90                    95

Ile Ala Ala Gly Val Phe His Asn Ser Leu Leu Pro Asp Thr Val His
         100                    105                   110

Ser Pro Ser Tyr Thr Val Glu Lys Leu Leu Glu Ser Phe Pro Asp Trp
         115                    120                 125

Arg Asp Thr Glu Tyr Phe Thr Phe Thr Asn Ile Thr Gly Glu Thr Ile
    130                   135                   140

Thr Thr Met Lys Leu Gly Phe Val Leu Arg Glu Asn Leu Phe Thr
145               150                   155                160

Lys Cys Thr Asp Gly Glu Tyr Glu Leu Ala Lys Met Val Met Arg Lys
             165                    170                 175

Gly Ser Leu Phe Gln Asn Val Leu Ala Gln Arg Pro Lys Phe Thr Glu
             180                    185                 190

Lys Gly Tyr Gly Ser Ile Lys Lys Val Tyr Ile Trp Thr Asp Gln Asp
         195                    200                 205

Lys Ile Phe Leu Pro Asp Phe Gln Arg Trp Gln Ile Ala Asn Tyr Lys
    210                   215                   220

Pro Asp Lys Val Tyr Gln Val Gln Gly Gly Asp His Lys Leu Gln Leu
225               230                   235              240

Thr Lys Thr Glu Glu Val Ala His Ile Leu Gln Glu Val Ala Asp Ala
             245                    250                 255

Tyr Ala

<210> SEQ ID NO 2
<211> LENGTH: 777
<212> TYPE: DNA
<213> ORGANISM: Artificial Sequence
<220> FEATURE:
<223> OTHER INFORMATION: cassava cyanohydrin lyase

<400> SEQUENCE: 2

```
atggttactg cacacttcgt tctgattcac accatttgtc acggcgcatg gatttggcac      60
aaactgaaac cggccctgga acgtgctggc acaaagtta ctgcactgga catggcagcc     120
agtggcattg acccgcgtca aattgaacag atcaactctt cgatgaata ctctgaaccg     180
ctgctgactt tcctggaaaa actgccgcaa ggcgaaaagg ttatcattgt tggtgaaagc     240
tgtgcaggcc tgaacattgc tattgctgct gatcgttacg ttgacaaaat tgcagctggc     300
gttttccaca actccctgct gccggacacc gttcacagcc cgtcttacac tgttgaaaag     360
ctgctggaat cgttcccgga ctggcgtgac acagaatatt tcacgttcac caacatcact     420
ggcgaaacca tcactaccat gaaactgggt ttcgttctgc tgcgtgaaaa cctgttcacc     480
aaatgcactg atggcgaata tgaactggca aaaatggtta tgcgcaaggg ctctctgttc     540
caaaacgttc tggctcagcg tccgaagttc actgaaaaag gctacggctc tatcaagaaa     600
gtttatattt ggaccgatca agacaaaata ttcctgccgg acttccaacg ctggcaaatt     660
gcaaactaca aaccggacaa ggtttatcag gttcaaggcg gcgatcacaa gctgcagctg     720
acaaaaactg aagaagtagc tcacattctg caagaagttg ctgatgcata cgcttaa       777
```

<210> SEQ ID NO 3
<211> LENGTH: 33
<212> TYPE: DNA
<213> ORGANISM: Artificial Sequence

```
<220> FEATURE:
<223> OTHER INFORMATION: H103-f primer sequence
<220> FEATURE:
<221> NAME/KEY: misc_feature
<222> LOCATION: (16)..(18)
<223> OTHER INFORMATION: n is a, c, g, or t

<400> SEQUENCE: 3
gcagctggcg ttttcnnnaa ctccctgctg ccg                          33

<210> SEQ ID NO 4
<211> LENGTH: 33
<212> TYPE: DNA
<213> ORGANISM: Artificial Sequence
<220> FEATURE:
<223> OTHER INFORMATION: H103-r primer sequence
<220> FEATURE:
<221> NAME/KEY: misc_feature
<222> LOCATION: (16)..(18)
<223> OTHER INFORMATION: n is a, c, g, or t

<400> SEQUENCE: 4
cggcagcagg gagttnnnga aaacgccagc tgc                          33

<210> SEQ ID NO 5
<211> LENGTH: 33
<212> TYPE: DNA
<213> ORGANISM: Artificial Sequence
<220> FEATURE:
<223> OTHER INFORMATION: W128-f primer sequence
<220> FEATURE:
<221> NAME/KEY: misc_feature
<222> LOCATION: (16)..(18)
<223> OTHER INFORMATION: n is a, c, g, or t

<400> SEQUENCE: 5
gaatcgttcc cggacnnncg tgacacagaa tat                          33

<210> SEQ ID NO 6
<211> LENGTH: 33
<212> TYPE: DNA
<213> ORGANISM: Artificial Sequence
<220> FEATURE:
<223> OTHER INFORMATION: W128-r primer sequence
<220> FEATURE:
<221> NAME/KEY: misc_feature
<222> LOCATION: (16)..(18)
<223> OTHER INFORMATION: n is a, c, g, or t

<400> SEQUENCE: 6
atattctgtg tcacgnnngt ccgggaacga ttc                          33

<210> SEQ ID NO 7
<211> LENGTH: 33
<212> TYPE: DNA
<213> ORGANISM: Artificial Sequence
<220> FEATURE:
<223> OTHER INFORMATION: V2-f primer sequence
<220> FEATURE:
<221> NAME/KEY: misc_feature
<222> LOCATION: (16)..(18)
<223> OTHER INFORMATION: n is a, c, g, or t

<400> SEQUENCE: 7
ggagatatac atatgnnnac tgcacacttc gtt                          33

<210> SEQ ID NO 8
<211> LENGTH: 33
<212> TYPE: DNA
```

```
<213> ORGANISM: Artificial Sequence
<220> FEATURE:
<223> OTHER INFORMATION: V2-r primer sequence
<220> FEATURE:
<221> NAME/KEY: misc_feature
<222> LOCATION: (16)..(18)
<223> OTHER INFORMATION: n is a, c, g, or t

<400> SEQUENCE: 8
aacgaagtgt gcagtnnnca tatgtatatc tcc                                33

<210> SEQ ID NO 9
<211> LENGTH: 33
<212> TYPE: DNA
<213> ORGANISM: Artificial Sequence
<220> FEATURE:
<223> OTHER INFORMATION: L36-f primer sequence
<220> FEATURE:
<221> NAME/KEY: misc_feature
<222> LOCATION: (16)..(18)
<223> OTHER INFORMATION: n is a, c, g, or t

<400> SEQUENCE: 9
cacaaagtta ctgcannnga catggcagcc agt                                33

<210> SEQ ID NO 10
<211> LENGTH: 33
<212> TYPE: DNA
<213> ORGANISM: Artificial Sequence
<220> FEATURE:
<223> OTHER INFORMATION: L36-r primer sequence
<220> FEATURE:
<221> NAME/KEY: misc_feature
<222> LOCATION: (16)..(18)
<223> OTHER INFORMATION: n is a, c, g, or t

<400> SEQUENCE: 10
actggctgcc atgtcnnntg cagtaacttt gtg                                33

<210> SEQ ID NO 11
<211> LENGTH: 35
<212> TYPE: DNA
<213> ORGANISM: Artificial Sequence
<220> FEATURE:
<223> OTHER INFORMATION: C81-f primer sequence
<220> FEATURE:
<221> NAME/KEY: misc_feature
<222> LOCATION: (17)..(19)
<223> OTHER INFORMATION: n is a, c, g, or t

<400> SEQUENCE: 11
cattgttggt gaaagcnnng caggcctgaa cattg                              35

<210> SEQ ID NO 12
<211> LENGTH: 35
<212> TYPE: DNA
<213> ORGANISM: Artificial Sequence
<220> FEATURE:
<223> OTHER INFORMATION: C81-r primer sequence
<220> FEATURE:
<221> NAME/KEY: misc_feature
<222> LOCATION: (17)..(19)
<223> OTHER INFORMATION: n is a, c, g, or t

<400> SEQUENCE: 12
caatgttcag gcctgcnnng ctttcaccaa caatg                              35

<210> SEQ ID NO 13
<211> LENGTH: 33
```

```
<212> TYPE: DNA
<213> ORGANISM: Artificial Sequence
<220> FEATURE:
<223> OTHER INFORMATION: V94-f primer sequence
<220> FEATURE:
<221> NAME/KEY: misc_feature
<222> LOCATION: (16)..(18)
<223> OTHER INFORMATION: n is a, c, g, or t

<400> SEQUENCE: 13
gctgctgatc gttacnnnga caaaattgca gct                                33

<210> SEQ ID NO 14
<211> LENGTH: 33
<212> TYPE: DNA
<213> ORGANISM: Artificial Sequence
<220> FEATURE:
<223> OTHER INFORMATION: V94-r primer sequence
<220> FEATURE:
<221> NAME/KEY: misc_feature
<222> LOCATION: (16)..(18)
<223> OTHER INFORMATION: n is a, c, g, or t

<400> SEQUENCE: 14
agctgcaatt ttgtcnnngt aacgatcagc agc                                33

<210> SEQ ID NO 15
<211> LENGTH: 35
<212> TYPE: DNA
<213> ORGANISM: Artificial Sequence
<220> FEATURE:
<223> OTHER INFORMATION: L121-f primer sequence
<220> FEATURE:
<221> NAME/KEY: misc_feature
<222> LOCATION: (18)..(20)
<223> OTHER INFORMATION: n is a, c, g, or t

<400> SEQUENCE: 15
cttacactgt tgaaaagnnn ctggaatcgt tcccg                              35

<210> SEQ ID NO 16
<211> LENGTH: 35
<212> TYPE: DNA
<213> ORGANISM: Artificial Sequence
<220> FEATURE:
<223> OTHER INFORMATION: L121-r primer sequence
<220> FEATURE:
<221> NAME/KEY: misc_feature
<222> LOCATION: (16)..(18)
<223> OTHER INFORMATION: n is a, c, g, or t

<400> SEQUENCE: 16
cgggaacgat tccagnnnct tttcaacagt gtaag                              35

<210> SEQ ID NO 17
<211> LENGTH: 33
<212> TYPE: DNA
<213> ORGANISM: Artificial Sequence
<220> FEATURE:
<223> OTHER INFORMATION: L122-f primer sequence
<220> FEATURE:
<221> NAME/KEY: misc_feature
<222> LOCATION: (16)..(18)
<223> OTHER INFORMATION: n is a, c, g, or t

<400> SEQUENCE: 17
actgttgaaa agctgnnnga atcgttcccg gac                                33

<210> SEQ ID NO 18
```

```
<211> LENGTH: 33
<212> TYPE: DNA
<213> ORGANISM: Artificial Sequence
<220> FEATURE:
<223> OTHER INFORMATION: L122-r primer sequence
<220> FEATURE:
<221> NAME/KEY: misc_feature
<222> LOCATION: (16)..(18)
<223> OTHER INFORMATION: n is a, c, g, or t

<400> SEQUENCE: 18
gtccgggaac gattcnnnca gcttttcaac agt                              33

<210> SEQ ID NO 19
<211> LENGTH: 33
<212> TYPE: DNA
<213> ORGANISM: Artificial Sequence
<220> FEATURE:
<223> OTHER INFORMATION: F125-f primer sequence
<220> FEATURE:
<221> NAME/KEY: misc_feature
<222> LOCATION: (16)..(18)
<223> OTHER INFORMATION: n is a, c, g, or t

<400> SEQUENCE: 19
aagctgctgg aatcgnnncc ggactggcgt gac                              33

<210> SEQ ID NO 20
<211> LENGTH: 33
<212> TYPE: DNA
<213> ORGANISM: Artificial Sequence
<220> FEATURE:
<223> OTHER INFORMATION: F125-r primer sequence
<220> FEATURE:
<221> NAME/KEY: misc_feature
<222> LOCATION: (16)..(18)
<223> OTHER INFORMATION: n is a, c, g, or t

<400> SEQUENCE: 20
gtcacgccag tccggnnncg attccagcag ctt                              33

<210> SEQ ID NO 21
<211> LENGTH: 33
<212> TYPE: DNA
<213> ORGANISM: Artificial Sequence
<220> FEATURE:
<223> OTHER INFORMATION: D127-f primer sequence
<220> FEATURE:
<221> NAME/KEY: misc_feature
<222> LOCATION: (16)..(18)
<223> OTHER INFORMATION: n is a, c, g, or t

<400> SEQUENCE: 21
ctggaatcgt tcccgnnngc acgtgacaca gaa                              33

<210> SEQ ID NO 22
<211> LENGTH: 33
<212> TYPE: DNA
<213> ORGANISM: Artificial Sequence
<220> FEATURE:
<223> OTHER INFORMATION: D127-r primer sequence
<220> FEATURE:
<221> NAME/KEY: misc_feature
<222> LOCATION: (16)..(18)
<223> OTHER INFORMATION: n is a, c, g, or t

<400> SEQUENCE: 22
ttctgtgtca cgtgcnnncg ggaacgattc cag                              33
```

<210> SEQ ID NO 23
<211> LENGTH: 33
<212> TYPE: DNA
<213> ORGANISM: Artificial Sequence
<220> FEATURE:
<223> OTHER INFORMATION: R129-f primer sequence
<220> FEATURE:
<221> NAME/KEY: misc_feature
<222> LOCATION: (16)..(18)
<223> OTHER INFORMATION: n is a, c, g, or t

<400> SEQUENCE: 23
tcgttcccgg acgcannnga cacagaatat ttc                          33

<210> SEQ ID NO 24
<211> LENGTH: 33
<212> TYPE: DNA
<213> ORGANISM: Artificial Sequence
<220> FEATURE:
<223> OTHER INFORMATION: R129-r primer sequence
<220> FEATURE:
<221> NAME/KEY: misc_feature
<222> LOCATION: (16)..(18)
<223> OTHER INFORMATION: n is a, c, g, or t

<400> SEQUENCE: 24
gaaatattct gtgtcnnntg cgtccgggaa cga                          33

<210> SEQ ID NO 25
<211> LENGTH: 33
<212> TYPE: DNA
<213> ORGANISM: Artificial Sequence
<220> FEATURE:
<223> OTHER INFORMATION: T140-f primer sequence
<220> FEATURE:
<221> NAME/KEY: misc_feature
<222> LOCATION: (16)..(18)
<223> OTHER INFORMATION: n is a, c, g, or t

<400> SEQUENCE: 25
acgttcacca acatcnnngg cgaaaccatc act                          33

<210> SEQ ID NO 26
<211> LENGTH: 33
<212> TYPE: DNA
<213> ORGANISM: Artificial Sequence
<220> FEATURE:
<223> OTHER INFORMATION: T140-r primer sequence
<220> FEATURE:
<221> NAME/KEY: misc_feature
<222> LOCATION: (16)..(18)
<223> OTHER INFORMATION: n is a, c, g, or t

<400> SEQUENCE: 26
agtgatggtt tcgccnnnga tgttggtgaa cgt                          33

<210> SEQ ID NO 27
<211> LENGTH: 33
<212> TYPE: DNA
<213> ORGANISM: Artificial Sequence
<220> FEATURE:
<223> OTHER INFORMATION: M147-f primer sequence
<220> FEATURE:
<221> NAME/KEY: misc_feature
<222> LOCATION: (16)..(18)
<223> OTHER INFORMATION: n is a, c, g, or t

<400> SEQUENCE: 27
gaaaccatca ctaccnnnaa actgggtttc gtt                          33

```
<210> SEQ ID NO 28
<211> LENGTH: 33
<212> TYPE: DNA
<213> ORGANISM: Artificial Sequence
<220> FEATURE:
<223> OTHER INFORMATION: M147-r primer sequence
<220> FEATURE:
<221> NAME/KEY: misc_feature
<222> LOCATION: (16)..(18)
<223> OTHER INFORMATION: n is a, c, g, or t

<400> SEQUENCE: 28
aacgaaaccc agtttnnngg tagtgatggt ttc                                33

<210> SEQ ID NO 29
<211> LENGTH: 35
<212> TYPE: DNA
<213> ORGANISM: Artificial Sequence
<220> FEATURE:
<223> OTHER INFORMATION: L149-f primer sequence
<220> FEATURE:
<221> NAME/KEY: misc_feature
<222> LOCATION: (17)..(19)
<223> OTHER INFORMATION: n is a, c, g, or t

<400> SEQUENCE: 29
catcactacc atgaaannng gtttcgttct gctgc                              35

<210> SEQ ID NO 30
<211> LENGTH: 35
<212> TYPE: DNA
<213> ORGANISM: Artificial Sequence
<220> FEATURE:
<223> OTHER INFORMATION: L149-r primer sequence
<220> FEATURE:
<221> NAME/KEY: misc_feature
<222> LOCATION: (17)..(19)
<223> OTHER INFORMATION: n is a, c, g, or t

<400> SEQUENCE: 30
gcagcagaac gaaaccnnnt tcatggtag tgatg                               35

<210> SEQ ID NO 31
<211> LENGTH: 33
<212> TYPE: DNA
<213> ORGANISM: Artificial Sequence
<220> FEATURE:
<223> OTHER INFORMATION: G165-f primer sequence
<220> FEATURE:
<221> NAME/KEY: misc_feature
<222> LOCATION: (16)..(18)
<223> OTHER INFORMATION: n is a, c, g, or t

<400> SEQUENCE: 31
accaaatgca ctgatnnnga atatgaactg gca                                33

<210> SEQ ID NO 32
<211> LENGTH: 33
<212> TYPE: DNA
<213> ORGANISM: Artificial Sequence
<220> FEATURE:
<223> OTHER INFORMATION: G165-r primer sequence
<220> FEATURE:
<221> NAME/KEY: misc_feature
<222> LOCATION: (16)..(18)
<223> OTHER INFORMATION: n is a, c, g, or t

<400> SEQUENCE: 32
tgccagttca tattcnnnat cagtgcattt ggt                                33
```

<210> SEQ ID NO 33
<211> LENGTH: 33
<212> TYPE: DNA
<213> ORGANISM: Artificial Sequence
<220> FEATURE:
<223> OTHER INFORMATION: K176-f primer sequence
<220> FEATURE:
<221> NAME/KEY: misc_feature
<222> LOCATION: (16)..(18)
<223> OTHER INFORMATION: n is a, c, g, or t

<400> SEQUENCE: 33
gaactggcaa aaatgnnnat gcgcaagggc tct                                   33

<210> SEQ ID NO 34
<211> LENGTH: 33
<212> TYPE: DNA
<213> ORGANISM: Artificial Sequence
<220> FEATURE:
<223> OTHER INFORMATION: K176-r primer sequence
<220> FEATURE:
<221> NAME/KEY: misc_feature
<222> LOCATION: (16)..(18)
<223> OTHER INFORMATION: n is a, c, g, or t

<400> SEQUENCE: 34
agagcccttg cgcatnnnca tttttgccag ttc                                   33

<210> SEQ ID NO 35
<211> LENGTH: 38
<212> TYPE: DNA
<213> ORGANISM: Artificial Sequence
<220> FEATURE:
<223> OTHER INFORMATION: K176-f primer sequence
<220> FEATURE:
<221> NAME/KEY: misc_feature
<222> LOCATION: (18)..(20)
<223> OTHER INFORMATION: n is a, c, g, or t

<400> SEQUENCE: 35
caaaaatggt tatgcgcnnn ggctctctgt tccaaaac                              38

<210> SEQ ID NO 36
<211> LENGTH: 38
<212> TYPE: DNA
<213> ORGANISM: Artificial Sequence
<220> FEATURE:
<223> OTHER INFORMATION: K176-r primer sequence
<220> FEATURE:
<221> NAME/KEY: misc_feature
<222> LOCATION: (19)..(21)
<223> OTHER INFORMATION: n is a, c, g, or t

<400> SEQUENCE: 36
gttttggaac agagagccnn ngcgcataac cattttttg                              38

<210> SEQ ID NO 37
<211> LENGTH: 33
<212> TYPE: DNA
<213> ORGANISM: Artificial Sequence
<220> FEATURE:
<223> OTHER INFORMATION: K199-f primer sequence
<220> FEATURE:
<221> NAME/KEY: misc_feature
<222> LOCATION: (16)..(18)
<223> OTHER INFORMATION: n is a, c, g, or t

<400> SEQUENCE: 37
ggctacggct ctatcnnnaa agtttatatt tgg                                33

<210> SEQ ID NO 38
<211> LENGTH: 33
<212> TYPE: DNA
<213> ORGANISM: Artificial Sequence
<220> FEATURE:
<223> OTHER INFORMATION: K199-r primer sequence
<220> FEATURE:
<221> NAME/KEY: misc_feature
<222> LOCATION: (16)..(18)
<223> OTHER INFORMATION: n is a, c, g, or t

<400> SEQUENCE: 38
ccaaatataa actttnnnga tagagccgta gcc                                33

<210> SEQ ID NO 39
<211> LENGTH: 33
<212> TYPE: DNA
<213> ORGANISM: Artificial Sequence
<220> FEATURE:
<223> OTHER INFORMATION: K209-f primer sequence
<220> FEATURE:
<221> NAME/KEY: misc_feature
<222> LOCATION: (16)..(18)
<223> OTHER INFORMATION: n is a, c, g, or t

<400> SEQUENCE: 39
tggaccgatc aagacnnnat attcctgccg gac                                33

<210> SEQ ID NO 40
<211> LENGTH: 33
<212> TYPE: DNA
<213> ORGANISM: Artificial Sequence
<220> FEATURE:
<223> OTHER INFORMATION: K209-r primer sequence
<220> FEATURE:
<221> NAME/KEY: misc_feature
<222> LOCATION: (16)..(18)
<223> OTHER INFORMATION: n is a, c, g, or t

<400> SEQUENCE: 40
gtccggcagg aatatnnngt cttgatcggt cca                                33

<210> SEQ ID NO 41
<211> LENGTH: 33
<212> TYPE: DNA
<213> ORGANISM: Artificial Sequence
<220> FEATURE:
<223> OTHER INFORMATION: Q216-f primer sequence
<220> FEATURE:
<221> NAME/KEY: misc_feature
<222> LOCATION: (16)..(18)
<223> OTHER INFORMATION: n is a, c, g, or t

<400> SEQUENCE: 41
ttcctgccgg acttcnnncg ctggcaaatt gca                                33

<210> SEQ ID NO 42
<211> LENGTH: 33
<212> TYPE: DNA
<213> ORGANISM: Artificial Sequence
<220> FEATURE:
<223> OTHER INFORMATION: Q216-r primer sequence
<220> FEATURE:
<221> NAME/KEY: misc_feature
<222> LOCATION: (16)..(18)
<223> OTHER INFORMATION: n is a, c, g, or t

<400> SEQUENCE: 42

```
tgcaatttgc cagcgnnnga agtccggcag gaa                        33
```

<210> SEQ ID NO 43
<211> LENGTH: 34
<212> TYPE: DNA
<213> ORGANISM: Artificial Sequence
<220> FEATURE:
<223> OTHER INFORMATION: K224-f primer sequence
<220> FEATURE:
<221> NAME/KEY: misc_feature
<222> LOCATION: (16)..(18)
<223> OTHER INFORMATION: n is a, c, g, or t

<400> SEQUENCE: 43

```
caaattgcaa actacnnncc ggacaaggtt tatc                       34
```

<210> SEQ ID NO 44
<211> LENGTH: 34
<212> TYPE: DNA
<213> ORGANISM: Artificial Sequence
<220> FEATURE:
<223> OTHER INFORMATION: K224-r primer sequence
<220> FEATURE:
<221> NAME/KEY: misc_feature
<222> LOCATION: (17)..(19)
<223> OTHER INFORMATION: n is a, c, g, or t

<400> SEQUENCE: 44

```
gataaacctt gtccggnnng tagtttgcaa tttg                       34
```

<210> SEQ ID NO 45
<211> LENGTH: 38
<212> TYPE: DNA
<213> ORGANISM: Artificial Sequence
<220> FEATURE:
<223> OTHER INFORMATION: primer sequence
<220> FEATURE:
<221> NAME/KEY: misc_feature
<222> LOCATION: (18)..(20)
<223> OTHER INFORMATION: n is a, c, g, or t

<400> SEQUENCE: 45

```
caaaaatggt tatgcgcnnn ggctctctgt tccaaaac                   38
```

<210> SEQ ID NO 46
<211> LENGTH: 38
<212> TYPE: DNA
<213> ORGANISM: Artificial Sequence
<220> FEATURE:
<223> OTHER INFORMATION: primer sequence
<220> FEATURE:
<221> NAME/KEY: misc_feature
<222> LOCATION: (18)..(20)
<223> OTHER INFORMATION: n is a, c, g, or t

<400> SEQUENCE: 46

```
gtttttacca atacgcgnnn ccgagagaca aggttttg                   38
```